United States Patent [19]

Schumacher et al.

[11] 4,448,079

[45] May 15, 1984

[54] PROCESS FOR DETERMINING THE FORCE ACTING ON A TEST PIECE AND THE RESULTANT CHANGE IN PARAMETERS AND A DEVICE FOR CARRYING OUT SUCH A PROCESS

[75] Inventors: Gerd Schumacher, Pinneberg-Waldenau; Heinz-Werner Masurat, Pinneberg, both of Fed. Rep. of Germany

[73] Assignee: B.A.T. Cigaretten-Fabriken GmbH, Hamburg, Fed. Rep. of Germany

[21] Appl. No.: 359,912

[22] Filed: Mar. 19, 1982

[30] Foreign Application Priority Data

Mar. 23, 1981 [DE] Fed. Rep. of Germany ....... 3111319

[51] Int. Cl.³ .............................................. G01D 1/16
[52] U.S. Cl. .......................................... 73/789; 73/78
[58] Field of Search ................. 73/789, 790, 791, 792, 73/793, 78, 818, 821, 822, 823

[56] References Cited

U.S. PATENT DOCUMENTS 3,115,772  12/1963  O'Keeffe et al. .................... 73/78 X
3,558,866  1/1971   Poulson ............................ 73/791 X
3,948,091  4/1976   Voll ................................ 73/791 X

OTHER PUBLICATIONS

Untersuchungen mit einem verbesserten Densimeter zum Prufen der Fullfahigkeit von Schnittabak und der Harte von Cigaretten, Beitrage zur Tabakforschung.

*Primary Examiner*—Jerry W. Myracle
*Attorney, Agent, or Firm*—Finnegan, Henderson, Farabow, Garrett & Dunner

[57] ABSTRACT

To determine the force acting on a test piece and the resultant change in parameters, the test piece is subjected to linearly increasing force. The resultant change in parameters and the force needed for this purpose are measured continuously and compared with predetermined reference values for these two variables. As soon as equality is determined between at least one measured value and its associated reference value, the value pair under consideration, force/change in parameters, is detected. This process can be used for the measurement of various mechanical variables.

15 Claims, 5 Drawing Figures

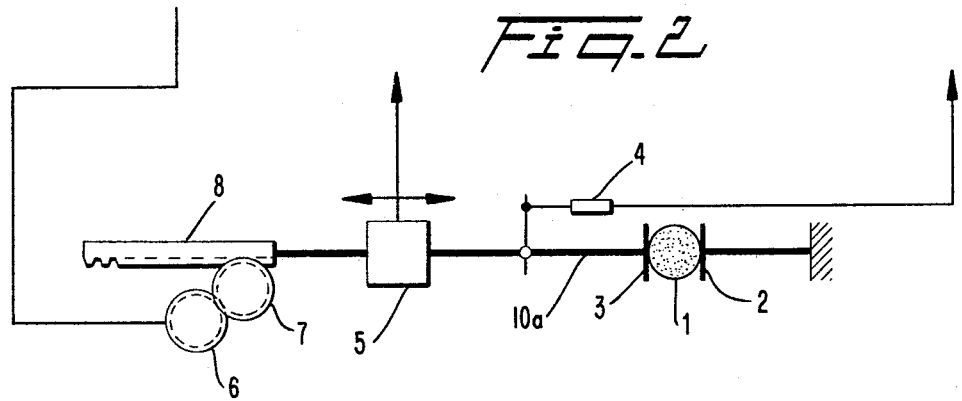
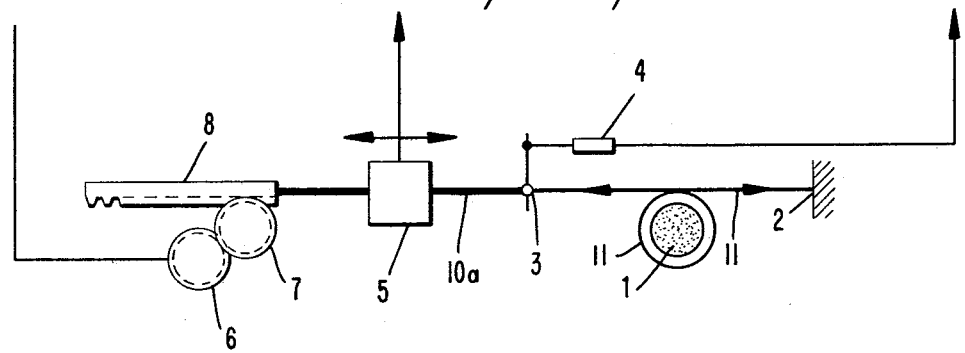
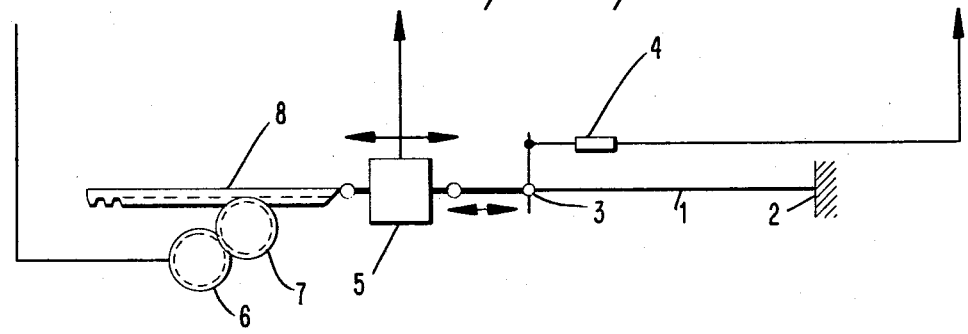
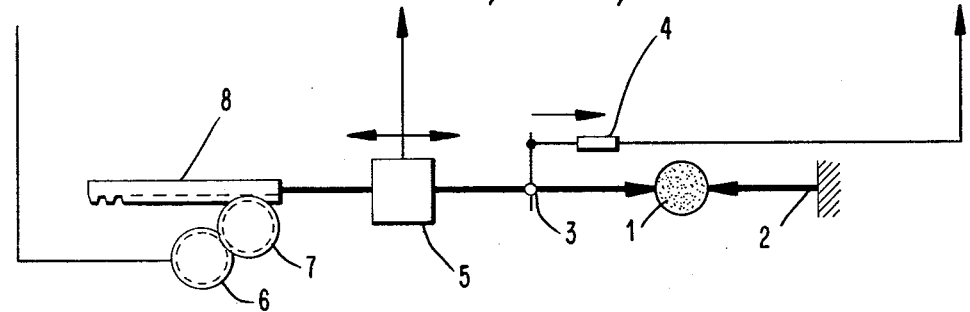

PROCESS FOR DETERMINING THE FORCE ACTING ON A TEST PIECE AND THE RESULTANT CHANGE IN PARAMETERS AND A DEVICE FOR CARRYING OUT SUCH A PROCESS

FIELD OF THE INVENTION

The invention relates to a process for determining the force acting on a test piece and the resultant change in the parameters of the test piece and to a device for carrying out such a process.

BACKGROUND OF THE INVENTION

The problems occuring when determining such values will be described below by means of measured variables which are particularly important in the cigarette industry. These include the tear strength of paper, for example cigarette paper, filter paper or tipping paper, the filling capacity of cut tobacco, the hardness of smokeable articles, for example cigarettes, filters, filter rods, cigarettes and cigarillos, as well as the diameter and the circumference of smokeable articles.

Various measuring heads and evaluating devices which are sometimes very expensive and are capable of measuring only a single variable are needed for measuring these variables.

A combination measuring instrument for the filling capacity of cut tobacco and the hardness of cigarettes is described in an article from "Beitrage zur Tabakforschung", Volume 4, Edition 7, December 1968, pages 293 et seq. To determine the filling capacity of cut tobacco, the column height of a defined weight of tobacco is measured after a predetermined time under a specific load while, to determine the hardness of smokeable articles, in particular cigarettes, the change in diameter of cigarettes is determined after a predetermined period under a specific load. The instrument described in this article combines both possibilities, and the instrument can be converted by exchanging the measuring heads.

However, this combination instrument itself has the disadvantage that the filling capacity as well as the hardness can be measured only under precisely predetermined and defined parameters, namely under a specific load. A change in the load is permitted only by extra, expensive conversion of the instrument.

SUMMARY OF THE INVENTION

The object of the invention is therefore to define a process for determining the force acting on a test piece and the resultant change in the parameters of the test piece as well as a device for carrying out such a process in which the above-mentioned disadvantages do not arise.

In particular, there should be discovered a process and device in which various parameters can be measured by the same basic principle merely by exchanging the respective measuring head.

These objects are achieved according to the invention by the features specified in the claims.

The advantages achieved with the invention are due to the following mode of operation: the test piece, for example cut tobacco, but also a smokeable article, is subjected to force which increases in a linear manner so that the cut tobacco but also the smokeable article are compressed. During this movement, the linear displacement and, at the same time, the force needed for it are measured, i.e. the counteracting force with which the test piece itself opposes the influence of external forces is determined.

The measured change in dimensions and the force needed for it are measured continuously and compared with predetermined reference values fed into an evaluating device beforehand. As soon as equality is determined between at least one measured value and its associated reference value, the measured value pair under consideration, i.e. force/change in dimension, is detected and delivered, for example displayed or printed out.

With this process it is possible not only to measure the force and/or the change in dimensions at precisely defined values, but at the same time also to detect and optionally deliver the characteristic curve for force/change in dimensions over a greater range, providing very accurate information about the behaviour of the test piece.

For example, the tear strength of paper, for example cigarette paper, filter paper or tipping paper, the filling capacity of cut tobacco, the hardness of smokeable articles, for example cigarettes, cigars, cigarillos, filters and filter rods, or the dimensions of smokeable articles, in particular the diameter or the circumference can be determined by this measuring principle using the same evaluating unit all the time and exchanging only the respective measuring head.

The important mechanical components of the measuring head are also the same, namely a driving mechanism for producing the continuous force, a force pick-up and a displacement transducer, only the gripping device for the respective test piece having to be exchanged. However, this gripping device can be exchanged by simple means, and the various holders for the test piece do not necessitate high expenditure either, resulting in a very simple but at the same time versatile measuring device.

To produce the linearly increasing force on the test piece there is used a driving mechanism with an electric motor which is adjusted via a control card from a sawtooth generator and thus yields a continuous movement.

In order to reduce the structural costs of the evaluating device, there is provided according to a preferred embodiment only a single comparator which is connected selectively to the displacement transducer and the force pick-up, only one of the respective instantaneous values under consideration for the two variables being compared with the associated reference value.

This comparator is connected to scanning and holding members capable of displaying the instantaneous values of both variables when there is equality between an instantaneous value and its associated reference value.

It is also possible to provide a recorder which records the two measured variables, namely the change in dimensions and the force needed for it, as a function of time.

BRIEF DESCRIPTION OF THE DRAWINGS

The invention is described in more detail below by means of embodiments with reference to the attached schematic drawings.

FIG. 2 is a detailed diagram of a measuring head device of FIG. 1 for determining the hardness of smokeable articles.

FIG. 3 is a detailed diagram of a measuring head for use with the electronic evaluating component of the device of FIG. 1 for determining the circumference of smokeable articles.

FIG. 4 is a detailed diagram of a measuring head for use with the electronic evaluating component of the device of FIG. 1 for determining the tear strength of paper.

FIG. 5 is a detailed diagram of a measuring head for use with the electronic evaluating component of the device of FIG. 1 for determining the diameter of smokeable articles.

Figure 1:
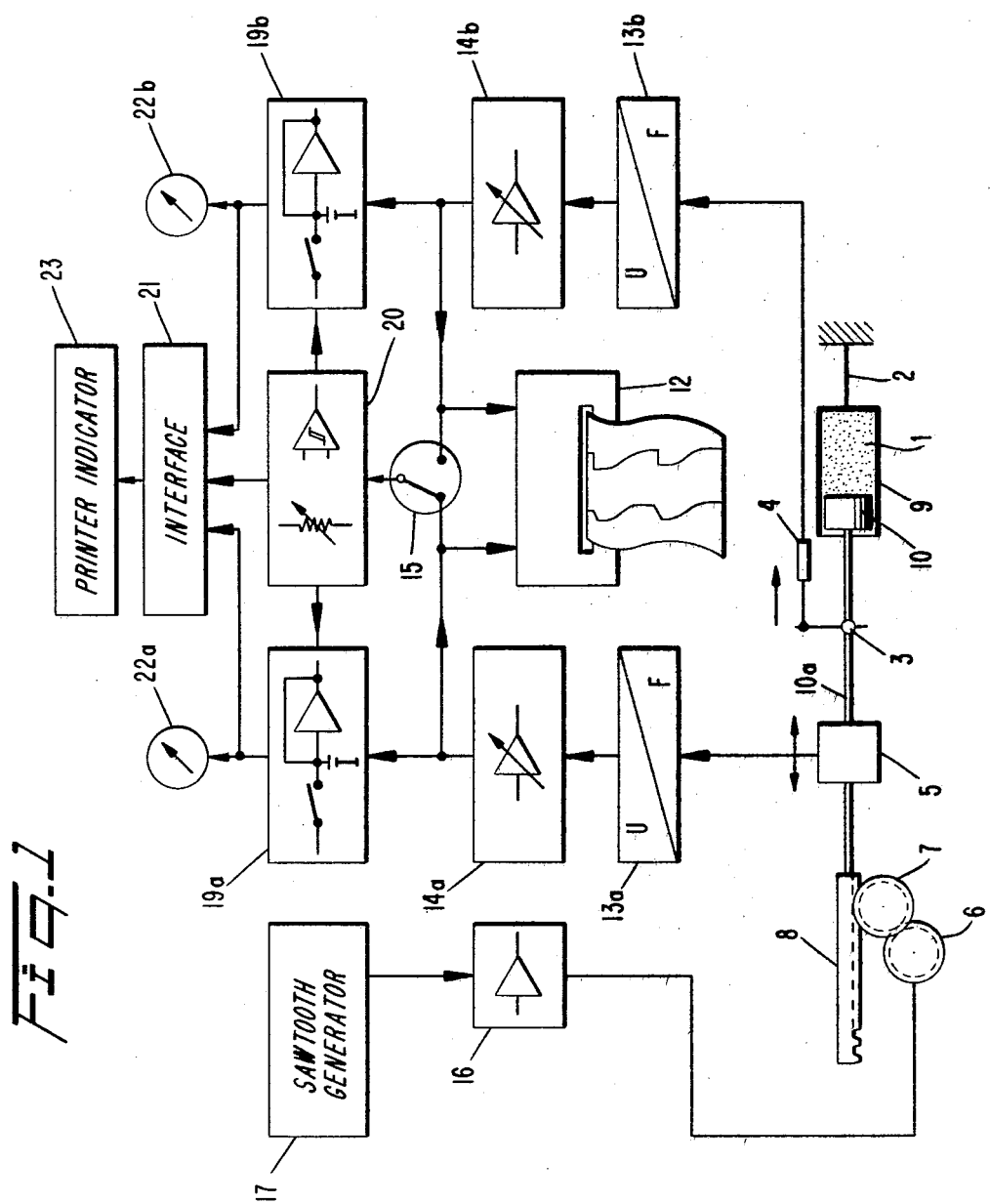
FIG. 1 is a schematic diagram showing a structure of a device according to the invention for determining the filling capacity of cut tobacco with the actual measuring head and the evaluating device.

The same reference numerals are used for the same respective structural elements in the following description. This also applies to the test piece which is always designated by the reference numeral 1 and which can be paper, in particular cigarette, filter or tipping paper, smokeable articles, i.e. cigars, cigarillos, cigarettes, filters or filter rods, or tobacco, in particular cut tobacco.

In the device according to FIG. 1, the test piece 1, cut tobacco in this case, is introduced into a hollow cylinder 9 which is arranged at one end on a stationary support 2 and is open at the other end. A piston 10 which can be moved by means of a rod 10a in the longitudinal direction of the cylinder 9 can be introduced through the open end into the interior of the hollow cylinder 9.

The rod 10a is displaced via an electric motor 6 which adjusts a toothed rack 8 connected to the rod 10a via a gear mechanism 7.

The electric motor 6 is supplied by a control card 16 which is controlled by a sawtooth generator 17.

An electric motor 6 thus rotates continuously in one direction under this control, the toothed rack 8 and therefore also the rod 10a and the piston 10 being displaced continuously in their longitudinal direction, to the right in the illustration in FIG. 1, so that the piston 10 is pressed, in turn, into the interior of the hollow cylinder 9.

A force pick-up 5 which takes up the load acting on the rod 10a and therefore, in the final analysis, on the cut tobacco 1, rests between the rod 10a and the toothed rack 8.

A displacement transducer 4 which detects the displacement of the rod during the movement of the piston 10 into the hollow cylinder 9 is also mounted on the rod 10a.

The counteracting force with which the test piece 1 itself opposes the influence of external forces produced by the electric motor 6 is therefore determined with this measuring arrangement.

The value appearing on the force pick-up 5 and the displacement transducer 4 is converted into a corresponding electrical signal via measured variable converters 13a and 13b respectively and, according to a preferred embodiment, into a corresponding voltage which is amplified by means of amplifiers 14a and 14b. These amplifiers 14a and 14b permit the electrical variables to be adapted in quantity to the measured variable. A recorder 12 connected downstream of the amplifiers 14a and 14b records the two measured variables as a function of time.

The output signals of the two amplifiers 14a, 14b are also transmitted, on the one hand, via a change-over switch 15 to a comparator 20 and, on the other hand, to scanning and holding members 19a, 19b which are controlled by the comparator 20.

The comparator compares selectively, i.e. under manual control via the switch 15, one of the two instantaneous values under consideration for the force exerted on the test piece 1 and the distance travelled by the piston 10 into the cylinder 9 with programmed reference values for these two measured variables and, when there is equality between at least one reference value and the associated instantaneous value, emits an output signal to the scanning and holding members 19a and 19b which then retain the instantaneous values of the measured variables.

The measured values detected in this way are displayed by separate displays 22a, 22b.

An interface 21 connected downstream of the scanning and holding members 19a, 19b and the comparator 20 processes the measured values, for example performs analog/digital conversion, and transmits the processed measured values to an output unit 23, for example a printer or a display unit.

When using this device for measuring purposes, the piston 10 is inserted into the hollow cylinder 9 continuously from left to right in the illustration in FIG. 1 and thus compresses the cut tobacco 1 which imposes a continuously increasing force against this movement as compression continues. The force exerted by the driving mechanism and the distance travelled by the piston 10 are determined continuously and compared with predetermined reference values in the manner described above so that the entire "characteristic curve for the filling capacity" i.e. the force to be applied for a specific degree of compression in the tobacco, and also, for specific predetermined measured points, the associated value pair, degree of compression in the cut tobacco/force exerted can be detected and printed out at the same time.

FIG. 2 shows a device for determining the hardness of smokeable articles, for example cigars, cigarillos, cigarettes, but also filters and filter rods. As the electronic evaluating component has the same structure as in the device shown in FIG. 1 for determining the filling capacity of cut tobacco, this structure is not illustrated again and will not be described again.

To determine the hardness, the smokeable article 1 is placed on one side on a stationary block 2 and on the other side on a moving block 3 which is connected via the rod 10a to the driving mechanism, of which only the electric motor 6, the gear mechanism 7 and the toothed rack 8 are shown. The rod 10a is again connected to the force pick-up 5 and the displacement transducer 4 which are each connected to the evaluating circuit according to FIG. 1.

During this measuring operation, the moving block 3 is displaced continuously from left to right towards the smokeable article 1, so it is possible to determine simultaneously the displacement and the force needed for this purpose and to compare with predetermined reference values and print or display in a similar manner as with the device according to FIG. 1.

FIG. 3 shows a device for determining the circumference of smokeable articles, the electronic evaluating circuit again not being shown. A thread 11 is looped round the circumference of the smokeable article 1. This thread is connected at one end to a stationary part 2 and at the other end to a moving part 3 which is coupled, in turn, via the rod 10a to the toothed rack 8. The displacement of the rod 10a is determined by means of the displacement transducer 4 and the force needed for this purpose by means of the force pick-up 5.

With this measuring head, the thread 11 and consequently also the rod 10a are pulled to the left according to the illustration in FIG. 3 and thus further tightened round the circumference of the smokeable article 1. When the loop of the thread 11 completely covers the external surface of the smokeable article 1, the force/distance curve exhibits a characteristic jump from which the circumference of this smokeable article 1 can be determined.

FIG. 4 shows the structure of a measuring head with which the tear strength of paper, in particular cigarette, filter or tipping paper, can be measured.

The paper 1 is arranged at one end on a stationary part 2 and at the other end on a moving part 3 which can be displaced via the driving mechanism to the left according to the illustration in FIG. 4.

The pulling force exerted on the paper during this movement is determined in the force pick-up 5 and the distance covered thereby is determined by the displacement transducer 4 and evaluated in the same manner as with the device according to FIG. 1.

As soon as the paper 1 tears, the value pair, force exerted/distance covered, exhibits a characteristic jump which is utilized for determining the exact tear strength of this paper.

Finally, FIG. 5 shows a measuring head of a device for determining the diameter of smokeable articles. As with the measuring head according to FIG. 2, the smokeable article 1 is placed on one side on a stationary block 2 and on the other side on a moving block 3 which are moved via the driving mechanism to the right according to the illustration in FIG. 5.

As the moving block 3 passes from free displacement and makes contact with the smokeable article 1, the force/distance graph shows a characteristic jump which can be used for determining the diameter of the smokeable article 1.

We claim:

1. A process for determining the force acting on a test piece and the parameters of the test piece reacting under the force, comprising the steps of:
   (a) exposing the test piece to the effect of the force increasing in a linear manner;
   (b) measuring continuously the resultant changes in parameters and the force needed for this purpose, and comparing the ascertained values with predetermined values; and
   (c) determining the measured value pair when there is equality between at least one measured value and the associated reference value.

2. A process according to claim 1 wherein said test piece includes a predetermined quantity of tobacco, and said step of exposing includes applying compression by a piston to the volume of said predetermined amount of tobacco for determining the filling capacity of said tobacco.

3. A process according to claim 1 wherein said test piece further comprises cigarette paper, filter paper or tipping paper, and said step of exposing includes gripping one end of said paper and applying a pulling force to the opposite end, for determining the changing length and tear strength of said paper.

4. A process according to claim 1 wherein said test piece is a smokeable article and said step of exposing includes pressing said smokeable article between a stationary block on one side and a moving block on the other side, for determining the hardness of the smokeable article and wherein said process measures the distance travelled by said moving block.

5. A process according to claim 1 wherein said test piece is a smokeable article and said step of exposing includes pressing said smokeable article between a stationary block on one side and a moving block on the other side, for determining the diameter of said smokeable article and wherein said process measures the jump in a force/displacement curve when said moving block impinges against said smokeable article.

6. A process according to claim 1 wherein said test piece is a smokeable article and said step of exposing includes looping thread around said smokeable article, said thread gripped securely at one end and attached to a moving block at the other end, for determining the circumference of the smokeable article and wherein said process measures the jump in a force/displacement curve when said thread impinges on the surface of said smokeable article.

7. A device for determining the force acting on a test piece and the parameters of the test piece reacting under the force, comprising means for applying a force to said test piece by a continuously moving part, a displacement transducer connected to the moving part, and a force pick-up for the load resulting from the force acting on the test piece.

8. A device according to claim 7 wherein said force applying means includes a driving motor, a gear mechanism, and a toothed rack, said toothed rack having one end connected by said force pick-up to said moving part, and said toothed rack being driven in a longitudinal direction by said motor through said gear mechanism.

9. A device according to claim 8, also including a sawtooth generator and a control card, said driving motor being supplied by said sawtooth generator through the control card.

10. A device according to claim 7 also including circuit arrangements for converting the force and displacement into corresponding electrical variables, wherein said circuit arrangements are connected to said force pick-up and said displacement transducer.

11. A device according to claim 10 also including amplifiers, scanning members, holding members, a change-over switch, and a comparator, and wherein said circuit arrangements are connected through said amplifiers to said scanning members and said holding members, and wherein said circuit arrangements are also connected through said amplifiers and said change-over switch to said comparator.

12. A device according to claim 11, having a recorder, wherein said recorder records instantaneous values of said force and displacement as a function of time.

13. A device according to claim 12, further comprising two separate displays for reading said recorded values.

14. A device according to any one of claims 7 through 13, wherein said applying means includes a cylinder and a piston in said cylinder, and wherein said test piece includes a predetermined quantity of tobacco inserted into said cylinder, whereby the filling capacity of the tobacco is determined by advancing the piston against the tobacco.

15. A device according to any one of claims 7 through 13, wherein said test piece includes a smokeable article and wherein said applying means includes a thread looped around said smokeable article, whereby the circumference of said smokeable article is determined by a jump in a force/displacement curve when said thread impinges on the surface of said smokeable article.

* * * * *